United States Patent
Calderon

(10) Patent No.: US 9,623,219 B2
(45) Date of Patent: Apr. 18, 2017

(54) SURGICAL DILATORS WITH TIPS HAVING CURVED TAPERS

(71) Applicant: Alfred E. Mann Foundation for Scientific Research, Santa Clarita, CA (US)

(72) Inventor: Joseph L. Calderon, Culver City, CA (US)

(73) Assignee: The Alfred E. Mann Foundation For Scientific Research, Santa Clarita, CA (US)

( * ) Notice: Subject to any disclaimer, the term of this patent is extended or adjusted under 35 U.S.C. 154(b) by 357 days.

(21) Appl. No.: 14/174,790

(22) Filed: Feb. 6, 2014

(65) Prior Publication Data

US 2014/0277073 A1    Sep. 18, 2014

Related U.S. Application Data

(60) Provisional application No. 61/783,088, filed on Mar. 14, 2013.

(51) Int. Cl.
*A61B 17/00* (2006.01)
*A61M 29/00* (2006.01)
*A61B 17/34* (2006.01)

(52) U.S. Cl.
CPC ......... *A61M 29/00* (2013.01); *A61B 17/3417* (2013.01); *A61B 2017/3456* (2013.01)

(58) Field of Classification Search
CPC ............... A61M 29/00; A61B 17/3417; A61B 2017/320044; A61B 2017/320056
See application file for complete search history.

(56) References Cited

U.S. PATENT DOCUMENTS

2010/0318112 A1* 12/2010 Smith .................... A61B 17/34
606/185

* cited by examiner

*Primary Examiner* — Melanie Tyson
(74) *Attorney, Agent, or Firm* — Oleh J. Zajac

(57) ABSTRACT

Surgical dilators with tips having curved tapers and with a minimal distance between the distal and proximal ends of the dilator tips provide for precision placement of miniature medical devices at a target area in a body with reduced insertion force. A contour of a longitudinal cross section of the dilator tip comprises a first convex portion extending from the distal end to a first interface; a concave portion extending from the first interface to a second interface; and a second convex portion extending from the second interface to a third interface at the proximal end. The first convex portion and the second convex portion are convex relative to an interior of the tip and the concave portion is concave relative to the interior of the tip.

23 Claims, 5 Drawing Sheets

US 9,623,219 B2

1

SURGICAL DILATORS WITH TIPS HAVING CURVED TAPERS

RELATED APPLICATIONS

This application claims the benefit under 35 USC 119(e) of U.S. provisional patent application No. 61/783,088 which was filed on Mar. 14, 2013, and which is hereby incorporated by reference in its entirety.

FIELD OF THE INVENTION

The invention relates in general to medical devices and more specifically to surgical dilators with tips having curved tapers.

BACKGROUND

Surgical dilators are generally used to insert medical devices at a target location within a body. Dilators pierce through the skin and enable the placement of the medical devices in proximity to a nerve or tissue. Dilators are frequently used with a hollow tube shaped sheath that envelops the dilator. A dilator and a sheath when packaged and sold together are frequently referred to as an Introducer Set and such a set can also include a guidewire, which slides through the hollow center of the dilator. These dilators utilize a long tapered tip for penetrating the tissue. Such tips have straight tapers with acute angles with respect to the longitudinal axis of the dilator, such as 5 to 10 degrees. The length of the tapered tip is typically at least several times larger than the outside diameter of the dilator, in order to minimize the insertion force needed to insert the dilator into living tissue. After insertion of the dilator tip to the desired location in the tissue of a body, the dilator is retracted and the sheath remains in position to provide a passageway for insertion of an object, such as a medical device, through the sheath to position the object at the desired location within the tissue. Due to the long tapered tip of a typical dilator, the distance between the distal end of the tapered tip and the sheath is undesirably large which can result in an imprecise placement of a medical device at a target location during insertion. One way to improve the precision of placement of a medical device with a dilator is to use a dilator with a shorter tapered tip, but using such a dilator requires a larger insertion force for the dilator as it enters into the tissue, which could cause tissue damage. Thus, there is a need for a dilator that provides a minimal distance between the distal end of the tip and the sheath and which also reduces the insertion force during penetration.

DETAILED DESCRIPTION

Figure 1:
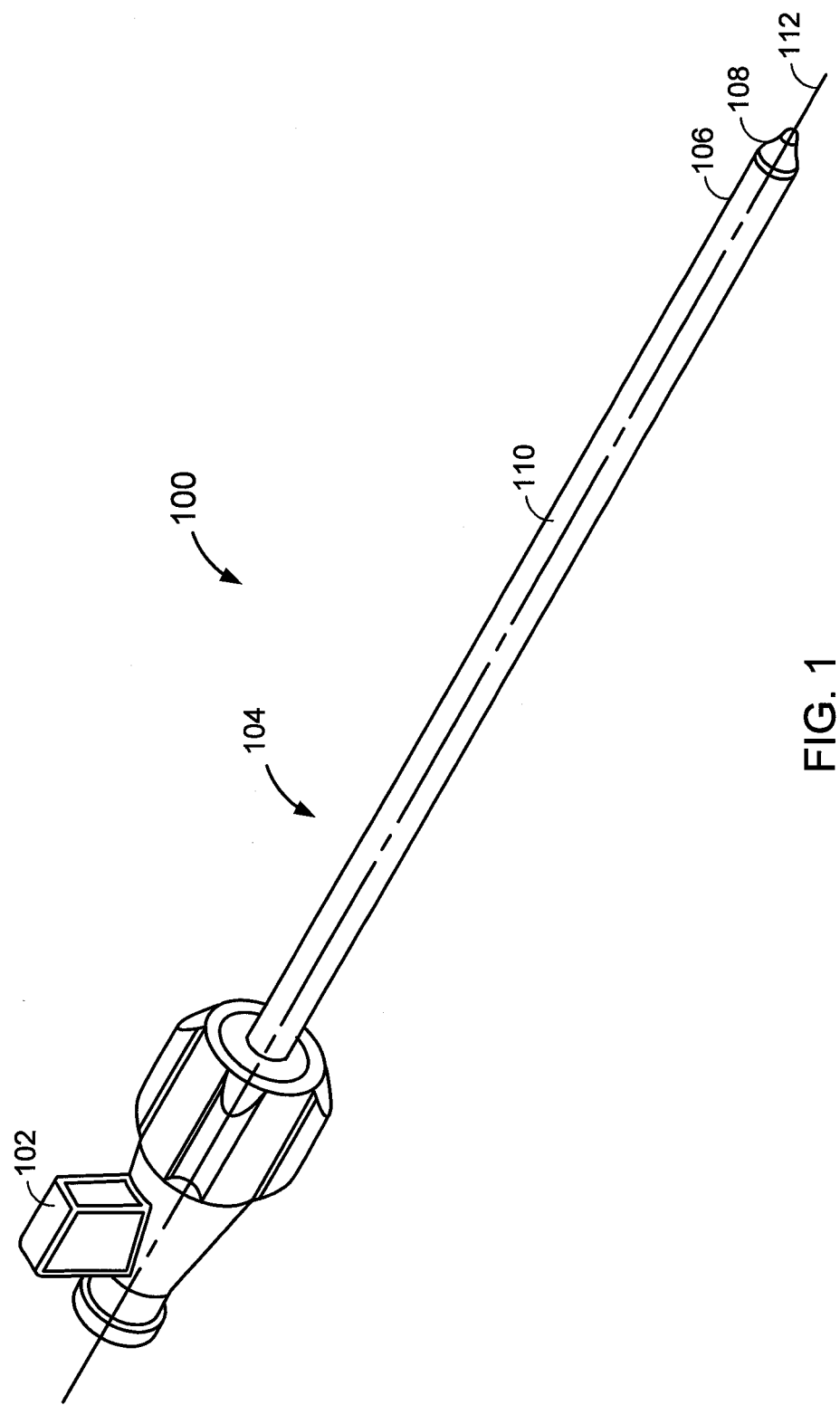
FIG. 1 is an illustration of a perspective view of an introducer set in accordance with the exemplary embodiment of the invention.

In accordance with the examples discussed herein, a surgical dilator tip having a minimal distance between the distal and proximal ends of the dilator tip provide for precision placement of miniature medical devices or medication at a target area in a body with reduced insertion force. In one example, a dilator comprises a dilator tip having a distal end, a proximal end and a circular lateral cross section having a radius increasing from a minor radius at the distal end to a major radius at the proximal end. A longitudinal contour of the dilator tip comprises a first convex portion extending from the distal end to a first interface; a concave portion extending from the first interface to a second interface; and a second convex portion extending from the second interface to a third interface at the proximal end. The first convex portion and the second convex portion are convex relative to an interior of the dilator tip and the concave portion is concave relative to the interior of the dilator.

Dilators are used for the implantation of medical devices such as stents, catheters, microstimulators or microsensors within the body of a patient. Microdevices such as microstimulators or microsensors are used to either sense signals from or provide stimulation signals to a nerve or tissue in a body. In order for a microdevice to be implanted successfully it has to be implanted at the target location. Accordingly, the accuracy of placement of the microdevice at the target location is of paramount importance. One of the ways to minimize the placement error is to use a dilator with a shorter tapered tip to minimize the distance between the distal end of the dilator tip and the distal end of the sheath. Commercially available dilators have relatively long angled tapered tips. As the diameter of the dilator is increased, however, the insertion forces are correspondingly increased. If the tapered portion of a dilator tip is shortened, then the insertion forces are also increased.

In the examples provided herein, the dilators of the present invention both reduce the insertion forces while at the same time maintain minimal distance between the distal end of the dilator tip and the distal end of the sheath. Also, in an example, a curved dilator tip provides transitional surfaces to minimize or eliminate any chances of tissue snagging during insertion or retrieval operations. Although the size of the inner diameter of the distal end of the tip may be close to conventional introducer sets, the shape of the outer surfaces of the tip is markedly different than conventional tips. In the three outer surfaces of the tip, a first surface is a first convex portion with a relatively small radius to dilate the tissue with minimal force. The second surface is a concave portion to dilate tissue to a larger diameter. Finally, the third surface is a second convex portion that completes the dilation of the tissue to a yet larger diameter. The interfaces between the portions of the tip facilitate smooth insertion.

FIG. 1 is an illustration of a perspective view of an introducer set 100 in accordance with the exemplary embodiment of the invention. As shown in FIG. 1, introducer set 100 includes handle 102 for grasping and directing the movement of the introducer set 100 within a body. Handle 102 is attached to and secures dilator 104. Sheath 106 slips over dilator 104 and may also be secured to handle 102. Dilator 104 includes curved dilator tip 108 at the end of dilator shaft 110. Dilator 104 is inside sheath 106 such that it can move within the sheath 106 along the longitudinal axis 112 of dilator 104 and sheath 106. During the use of introducer set 100, dilator tip 108 is pushed through the skin and into the tissue. Dilator shaft 110 and sheath 106 follow dilator tip 108 as it is pushed to the target location in the tissue. Typically, the dilator 104 is retracted leaving the sheath 106 in place within the tissue to allow insertion of an object or substance.

Figure 2A:
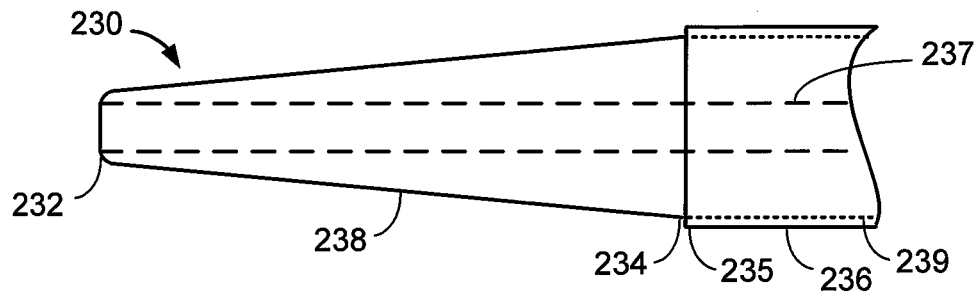
FIG. 2A is an illustration of a side view of the distal end of a prior art dilator with a long tip with a straight taper.

FIG. 2A is an illustration of a side view of the distal end of a prior art dilator 230 with a long tip 238. Tip 238 has a straight taper between its distal end 232 and its proximal end 234. FIG. 2A also shows sheath 236, which slides over the cylindrical portion 239 of dilator 230. Dilator 230 contains within it Internal channel 237. The distal end 235 of sheath 236 is shown positioned adjacent to the proximal end 234 of tapered tip 238. Dilator tip 238 has an acute angle of about 10 degrees. As dilator 230 is inserted into tissue, the long tapered tip 238 of dilator 230 results in a relatively smooth dilation of tissue without the use of excessive insertion force. After dilator 230 is inserted into a desired location in the tissue, dilator 230 is removed and the sheath 236 is left inserted in the tissue so that the inner channel 237 of sheath 236 can be used to deliver a medical microdevice into the space formed by dilator 230. However, the long tapered space formed in the tissue by the insertion of dilator 230 can result in the imprecise placement of a medical microdevice inserted using sheath 236.

Figure 2B:
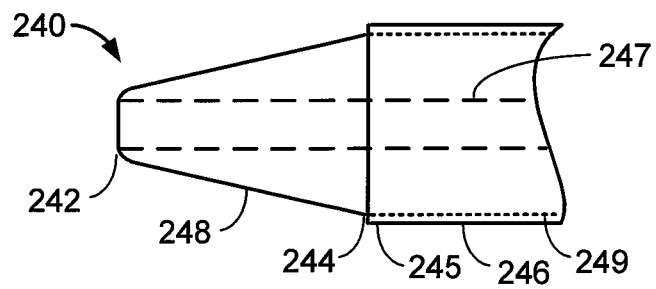
FIG. 2B is an illustration of a side view of the distal end of a prior art dilator with a short tip with a straight taper.

FIG. 2B is an illustration of a side view of the distal end of prior art dilator 240 with short tip 248. Tip 248 has a straight taper between its distal end 242 and its proximal end 234. FIG. 2B also shows sheath 246, which slides over the cylindrical portion 249 of dilator 240. FIG. 2B shows internal channel 247 within the cylindrical portion 249 of dilator 240. The distal end 245 of sheath 246 is shown positioned adjacent to the proximal end 244 of tapered tip 248. Dilator tip 248 has an angle of about 25 degrees, which gives dilator 240 a shorter tip 248 as compared to dilator 230 with its longer tip 238 as shown in FIG. 2A. As dilator 240 is inserted into tissue, the short tapered tip 248 of dilator 240 results in a dilation of tissue, but this can require a larger insertion force, as compared to using dilator 230 shown in FIG. 2A. After dilator 240 is inserted into a desired location in the tissue, the dilator 240 is removed and sheath 247 is left inserted in the tissue so that the inner channel of sheath 247 can be used to deliver a medical microdevice into the space formed by dilator 240. The short tapered space formed in the tissue by the insertion of dilator 240 can result in a more precise placement of a medical microdevice inserted using sheath 247, but the dilation of tissue requires a larger insertion force, as compared to the use of dilator 230 of FIG. 2A.

Figure 2C:
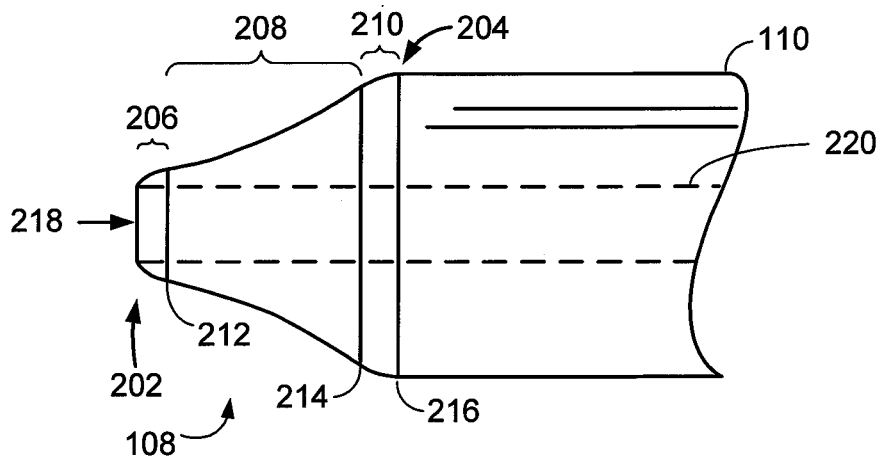
FIG. 2C is an illustration of a side view of the distal end of a dilator including the dilator tip with a curved taper in accordance with the exemplary embodiment of the invention.
Figure 3A:
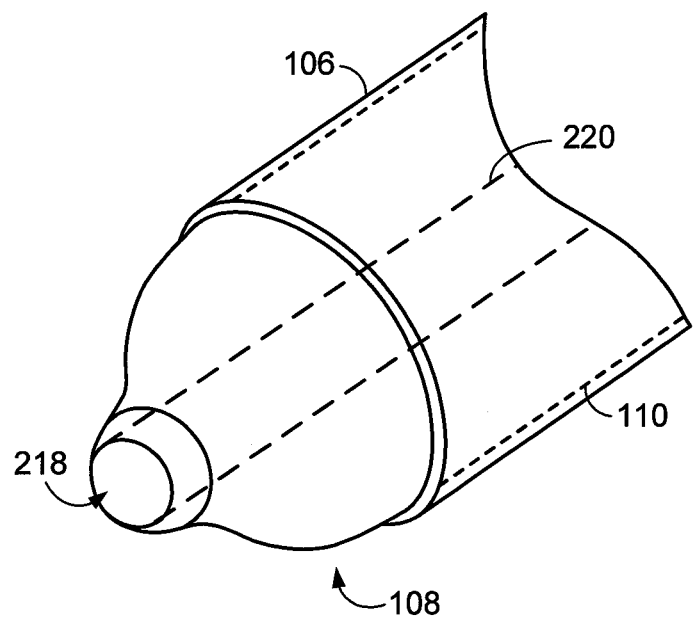
FIG. 3A is an illustration of a perspective view of the distal end of a dilator with a sheath in accordance with the exemplary embodiment of the invention.
Figure 3B:
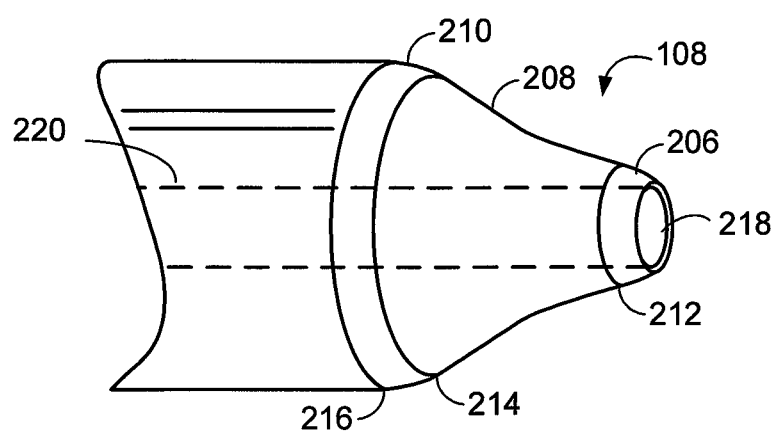
FIG. 3B is an illustration of a perspective view of the distal end of a dilator in accordance with the exemplary embodiment of the invention.
Figure 4:
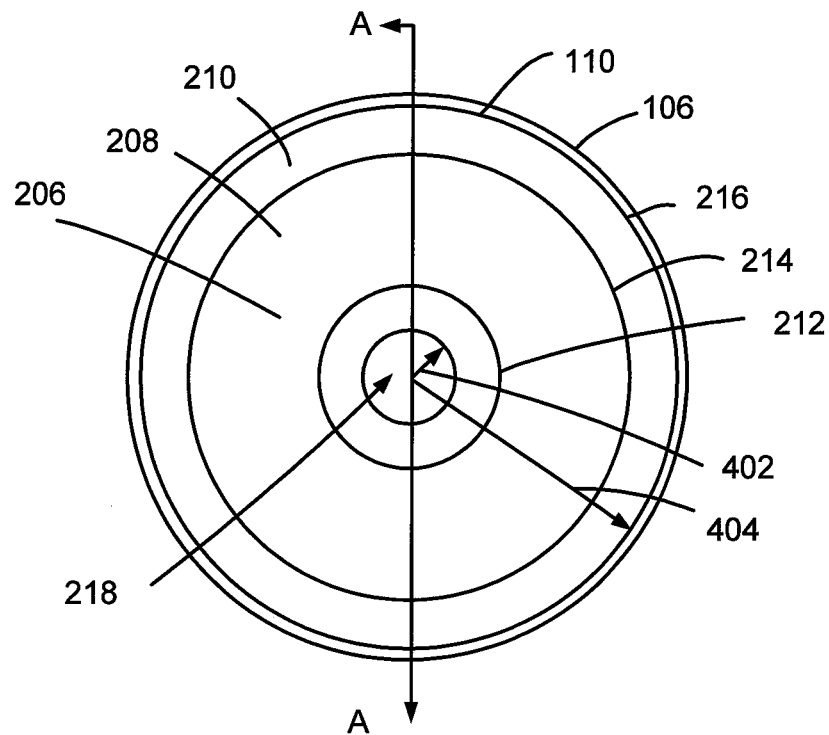
FIG. 4 is an illustration of a front view of the distal end of a dilator in accordance with the exemplary embodiment of the invention.
Figure 6:
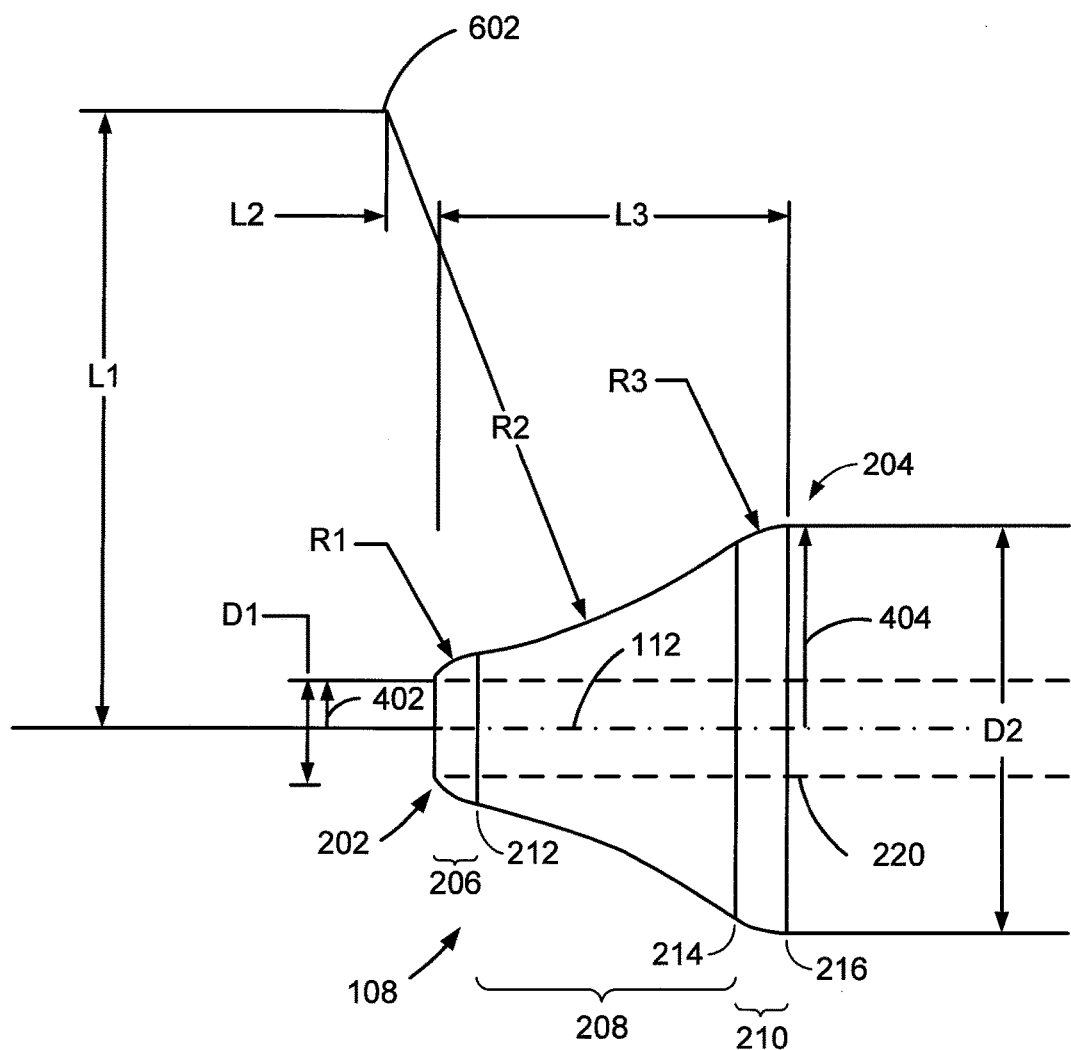
FIG. 6 is an illustration of a side view of a dilator tip showing the radii of the three portions of the dilator tip in accordance with the exemplary embodiment of the invention.

FIG. 2C is an illustration of a side view, FIG. 3A and FIG. 3B are illustrations of perspective views, FIG. 4 is a front view of the distal end of insertion set 100 including dilator tip 108 with a curved taper in accordance with the exemplary embodiment of the invention. FIG. 3A and FIG. 4 show the sheath 106 while FIG. 3B does not. Dilator tip 108 has distal end 202 and proximal end 204. Distal end 202 constitutes the point at which the tip 108 comes into contact with and penetrates the skin or tissue. Dilator tip 108 is joined to the dilator shaft 110 at the proximal end 204. Dilator shaft 110 is the rest of the elongated cylindrical portion of dilator 104. Dilator tip 108 has three curved portions 206, 208 and 210 connected at three interfaces 212, 214 and 216. The positions of the interfaces 212, 214 and 216 are indicated in FIG. 2C and FIG. 3B. A first portion at the distal end 202 of tip 108 is a convex portion 206 that joins a concave portion 208 at the first interface 212. The concave portion 208 joins the second convex portion 210 at the second interface 214. The second convex portion 210 joins the shaft 110 at the third interface 216, which is at the proximal end 204 of tip 108. Accordingly, the different contours of the portions 206, 208 and 210 and the shaft 110 merge together at the interfaces such that there are no discontinuities along the complete contour from the distal end 202 to the proximal end 204 of dilator tip 108. When viewed along the surface of a longitudinal cross section of the tip 108, such as shown in FIGS. 2C and 6, curved portions 206, 208 and 210 are respectively, convex, concave and convex relative to the interior of tip 108.

In the exemplary embodiment, tip 108 is formed from a single piece of material and as a result, tip 108 is a continuous structure and the curved portions 206, 208 and 210 are not discrete elements that are joined together. In some circumstances, however, the dilator tip 108 may be formed by fusing, gluing, or otherwise joining, one or more of the portions or sections of tip 108. Dilator tip 108 may be formed using any combination of techniques and materials. An example of a suitable technique includes forming the tip 108 from a biocompatible plastic using a die that is heated to the melting temperature of the plastic. A core section of plastic having the appropriate general dimensions is guided into the die for a few seconds to shape the plastic to form the tip 108 with the desired contour and dimensions. Dilator 104 with tip 108 may also be made from biocompatible metals and machined using machine tools.

Figure 5:
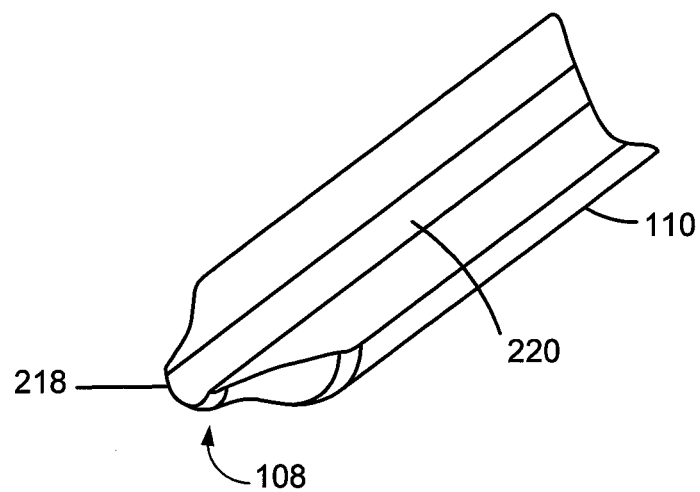
FIG. 5 is an illustration of a perspective view of a longitudinal cross section taken at line A-A of FIG. 4 of the distal end of a dilator including a dilator tip in accordance with the exemplary embodiment.

Although dilator tip 108 may be solid, dilator tip 108 includes an opening to a longitudinal channel in dilator 104. FIG. 5 is an illustration of a perspective view of a longitudinal cross section taken at line A-A of FIG. 4 of the distal end 202 of dilator 104 including dilator tip 108 in accordance with the exemplary embodiment. Dilator tip 108 includes an opening 218 to a channel 220 that spans the length of dilator 104 from the distal end 202 of the tip 108 through the shaft 110. Channel 220 allows injection and/or extraction of liquids into/from the tissue during and after the insertion process. For example, saline solutions may be injected to provide additional lubrication during the insertion of dilator 104 through the tissue. In some circumstances, channel 220 and opening 218 may be omitted. Channel 220 can also be used a passage for a guide wire, which is not shown in the figures.

As shown in FIG. 4, the lateral cross sections of tip 108 and shaft 110 are cylindrical. Accordingly, the curved portions 206, 208 and 210 and the interfaces 212, 214 and 216 are circular in lateral cross sectional contour. The radius of tip 108 increases from the distal end 202 to the shaft 110 in accordance with the cross sectional contour. As discussed further below, the contour is selected to minimize insertion force, snagging of tissue as well as the distance from the distal end 202 to the proximal end 204, which is adjacent to the distal end of sheath 106.

The distal end 202 of insertion set 100, starting with dilator 104 with tip 108, is inserted through tissue to begin the insertion process. Typically, the tissue includes skin and therefore the 108 is first inserted through the skin. For the examples, the relatively small radius and convex contour of the first convex portion 206 facilitates penetration of the tissue with reduced force, as compared to typical dilator tips with straight tapers, like dilator 230 shown in FIG. 2A. As the dilator 104 is further inserted, the concave portion 208 of the curved dilator tip 108 allows for an increase in radius within a short insertion distance while still minimizing insertion force. Insertion set 100 including dilator 104 is inserted into the tissue until the sheath 106 is positioned at, or adjacent to, the target location within the tissue. When the insertion object is a microdevice or other similar medical device, the target location is the area within the tissue where the insertion object will be placed.

As shown in FIGS. 4 and 6, dilator tip 108 expands from a minor radius 402 at the distal end 202 over the three portions to the proximal end 204 where the radius is a major radius 404. The first convex portion 206 initially comes into contact with the tissue and pierces through with minimal force. A first interface 212 contiguously connects the first convex portion 206 and the concave portion 208. The first interface 212 enables a smooth transition between the first convex portion 206 and the concave portion 208. The first interface 212 provides for a change in the shape and radius between the first convex portion 206 and the concave portion 208 and is the inflection point between a convex surface contour and the concave surface contour. The shape and radius of the concave portion 208 allows the tissue to gradually dilate as the tip 108 penetrates through the tissue. As the concave portion 208 expands toward the proximal end 204, it terminates at a second interface 214 for transition to the second convex portion 210. Similar to the first interface 212, the second interface 214 provides for a change in the radius and the shape between the concave portion 208 and the second convex portion 210. The second interface 214 is the inflection point between the concave surface contour and the convex surface contour. The second convex portion 210 is the final and the third surface that terminates at the third interface 216. The third interface 216 signifies the proximal end 204 of tip 108 having the major radius 404. Curved dilator tip 108 has a taper of three curved portions 206, 208 and 210, and has a circular lateral cross section with a radius that increases from a minor radius 402 at the distal end 202 to a major radius 404 at the proximal end 204. In this example, the elongated cylindrical portion 110 of dilator 104 maintains the major radius 404 along the shaft 110 from the proximal end 204 of the tip 108 to the handle 102. In some circumstances, the radius of the elongated cylindrical portion 110 of dilator 104 may vary depending on the application of the dilation insertion device.

FIG. 6 is an illustration of a longitudinal side view showing the radii of the three curved portions 206, 208 and 210 of tip 108 of dilator 104 in accordance with the exemplary embodiment of the invention. The longitudinal contour of tip 108 comprises a first convex portion 206 having a first radius, R1, which extends from the distal end 202 to the first interface 212. The concave portion 208 has a second radius R2, different than the first radius R1. The second radius R2 is referenced from a point 602 that is at a first length L1 from a center axis 112 of the tip and a second length L2 from the distal end 202 of tip 108.

The second convex portion 210 has a third radius R3, which is different from the first radius R1 and the second radius R2. The concave portion 208 has a proportionally larger second radius R2 than the first radius R1 and the third radius R3. The proportionality of the second radius R2 relative to the first radius R1 and the third radius R3 determines the distance between the distal end 202 and the proximal end 204 of tip 108.

The distance from the distal end 202 to the proximal end 204 is a third length L3. The inside diameter D1, is twice the minor radius 402. The outside diameter D2 is twice the major radius 404. The selection of R1, R2, R3, D1, D2, L1, L2, and L3 is based on the particular implementation of curved dilator tip 108 and its intended purpose. At least some of the dimensions are interdependent and selected to minimize the third length L3, while maintaining a smooth transition between the different curved portions 206, 208 and 210.

Dimensions are selected so that the distance between the distal end 202 of tip 108 of dilator 104 to the distal edge 204 of the dilator shaft 110 is minimized while maintaining low insertion forces. The second radius R2 of the concave portion 208 is between five to ten times the first radius R1 of the first convex portion 206 and is between five to ten times the third radius R3 of the third convex portion 210. In some circumstances, the second radius R2 of the concave portion 208 is between seven and eight times the first radius R1 of the first convex portion 206 and is between 6.5 and 7.5 times the third radius R3 of the second convex portion 210. In other embodiments, the second radius R2 of the concave portion 208 is between 7.3 and 7.5 times the first radius R1 of the first convex portion 206 and is between 6.8 and 7.1 times the third radius R3 of the second convex portion 210. An example of a suitable relationship between the radii includes the second radius being 7.39 times the first radius and 6.9 times the third radius. Therefore, examples of R1, R2, R3, D1, D2, L1, L2, and L3 include 0.028, 0.207, 0.030, 0.038, 0.144, 0.231, 0.020, and 0.124 inches, respectively. The length L3 of the dilator tip 108 is less than or equal to the outside diameter D2 of dilator 104.

In contrast to conventional dilator tips with straight tapers, such as those shown in FIGS. 2A and 2B, in the examples of the present invention, the convex and concave shapes of each of the surfaces with their associated radii provide for minimal distance between the distal end 202 and the proximal end 204 of tip 108. Also, dilator 104 in this example provides for reduced insertion force while minimizing or eliminating the snagging of the tissue.

Clearly, other embodiments and modifications of this invention will occur readily to those of ordinary skill in the art in view of these teachings. The above description is illustrative and not restrictive. This invention is to be limited only by the following claims, which include all such embodiments and modifications when viewed in conjunction with the above specification and accompanying drawings. The scope of the invention should, therefore, be determined not with reference to the above description, but instead should be determined with reference to the appended claims along with their full scope of equivalents.

What is claimed is:

1. A dilator comprising:
   a dilator tip having a distal end, a proximal end and a circular lateral cross section having a radius increasing from a minor radius at the distal end to a major radius at the proximal end, wherein a longitudinal contour of the tip comprises:
   a first convex portion extending from the distal end to a first interface;
   a concave portion extending from the first interface to a second interface; and a second convex portion extending from the second interface to a third interface at the proximal end, wherein the first convex portion and the second convex portion are convex relative to an interior of the tip and the concave portion is concave relative to the interior of the tip; wherein the length from the distal end to the proximal end is less than or equal to the diameter at the proximal end.

2. The dilator of claim 1, wherein the first convex portion and the concave portion are contiguously connected through the first interface.

3. The dilator of claim 1, wherein the second convex portion is contiguously connected to the concave portion through the second interface.

4. The dilator of claim 1, wherein the second convex portion terminates at the third interface, the dilator tip having the major radius at the third interface.

5. The dilator of claim 1, wherein a first radius of the first convex portion is less than a second radius of the concave portion.

6. The dilator of claim 5, wherein a third radius of the second convex portion is less than the second radius of the concave portion.

7. The dilator of claim 6, wherein the second radius is between five and ten times the first radius and between five and ten times the third radius.

8. The dilator of claim 6, wherein the second radius is between seven to eight times the first radius and between 6.5 and 7.5 times the third radius.

9. The dilator of claim 6, wherein the second radius is between 7.3 and 7.5 times the first radius and between 6.8 and 7.1 time the third radius.

10. The dilator of claim 6, wherein the second radius is 7.39 times the first radius and 6.9 times the third radius.

11. The dilator of claim 6, wherein the first radius is 0.028 inches, the second radius is 0.207 inches, and the third radius is 0.030 inches.

12. The dilator of claim 11, wherein a length from the distal end of the dilator tip to the proximal end of the dilator tip is 0.124 inches and the diameter at the proximal end of the dilator tip is 0.144 inches.

13. The dilator of claim 1, further comprising a dilator shaft, wherein the second convex portion is contiguously connected to the dilator shaft through the third interface.

14. The dilator of claim 13, further comprising a sheath, wherein the dilator shaft moves within the sheath.

15. The dilator of claim 14, further comprising a handle, wherein the handle is releasably coupled to the dilator, the sheath or both the dilator and the sheath.

16. An apparatus comprising:
a dilator tip having a distal end and a proximal end:
a dilator shaft connected to the proximal end,
the dilator tip having a circular lateral cross section having a radius increasing from a minor radius at the distal end to a major radius at the proximal end, wherein a longitudinal contour of the tip comprises:
a first convex portion extending from the distal end to a first interface;
a concave portion extending from the first interface to a second interface and contiguously connected through the first interface to the first convex portion; and
a second convex portion extending from the second interface to a third interface at the proximal end and contiguously connected to the concave portion through the second interface, wherein the second convex portion is contiguously connected to the dilator shaft through the third interface and wherein the first convex portion and the second convex portion are convex relative to an interior of the dilator tip and the concave portion is concave relative to the interior of the dilator tip; wherein a first radius of the first convex portion is less than a second radius of the concave portion, a third radius of the second convex portion is less than the second radius and wherein the second radius is between five and ten times the first radius and between five and ten times the third radius.

17. The apparatus of claim 16, wherein the second radius is between seven and eight times the first radius and is between 6.5 and 7.5 times the third radius.

18. The apparatus of claim 17, wherein the second radius is between 7.3 and 7.5 times the first radius and between 6.8 and 7.1 time the third radius.

19. The apparatus of claim 18, wherein the second radius is 7.39 times the first radius and 6.9 times the third radius.

20. The apparatus of claim 19, wherein the first radius is 0.028 inches, the second radius is 0.207 inches, and the third radius is 0.030 inches.

21. The apparatus of claim 20, wherein a length from the distal end to the proximal end is 0.124 inches.

22. The apparatus of claim 16, further comprising a sheath, wherein the dilator shaft moves within the sheath.

23. The apparatus of claim 22, further comprising a handle, wherein the handle is releasably coupled to either the dilator shaft, the sheath or both.

* * * * *

UNITED STATES PATENT AND TRADEMARK OFFICE
CERTIFICATE OF CORRECTION

PATENT NO.       : 9,623,219 B2
APPLICATION NO.  : 14/174790
DATED            : April 18, 2017
INVENTOR(S)      : Calderon It is certified that error appears in the above-identified patent and that said Letters Patent is hereby corrected as shown below:

On the Title Page

Item [71] to read as follows:
[71] Applicant: The Alfred E. Mann Foundation For Scientific Research Signed and Sealed this
Twenty-first Day of November, 2017

Joseph Matal
*Performing the Functions and Duties of the*
*Under Secretary of Commerce for Intellectual Property and*
*Director of the United States Patent and Trademark Office*